United States Patent [19]
Olson et al.

[11] Patent Number: 5,484,439
[45] Date of Patent: Jan. 16, 1996

[54] MODULAR FEMUR FIXATION DEVICE

[75] Inventors: C. Donald Olson, Palos Verdes; Mark G. Urbanski, Indian Wells, both of Calif.

[73] Assignee: Alphatec Manufacturing, Inc., Palm Desert, Calif.

[21] Appl. No.: 233,037

[22] Filed: Apr. 25, 1994

Related U.S. Application Data

[63] Continuation of Ser. No. 946,742, Sep. 16, 1992, abandoned.

[51] Int. Cl.⁶ ..................................................... A61F 5/00
[52] U.S. Cl. ................................. 606/65; 606/71; 606/67; 623/16
[58] Field of Search .................................. 623/16, 18, 19, 623/23, 17; 606/67, 68, 69, 70, 71, 72

[56] References Cited

U.S. PATENT DOCUMENTS

| | | |
|---|---|---|
| 2,381,050 | 8/1945 | Hardinge . |
| 2,486,303 | 10/1949 | Longfellow . |
| 2,561,550 | 7/1951 | Wright . |
| 2,702,543 | 2/1955 | Pugh et al. ............................ 606/65 |
| 3,374,786 | 3/1968 | Callender, Jr. . |
| 3,433,220 | 3/1969 | Zickel . |
| 3,439,671 | 4/1969 | Kuntscher . |
| 3,561,437 | 2/1971 | Orlich . |
| 3,596,656 | 8/1971 | Kaute . |
| 3,659,595 | 5/1972 | Haboush . |
| 3,782,374 | 1/1974 | Fischer . |
| 3,842,825 | 10/1974 | Wagner . |
| 4,009,712 | 3/1977 | Burstein et al. . |
| 4,040,129 | 8/1977 | Steinemann et al. . |
| 4,262,665 | 4/1981 | Roalstad et al. . |
| 4,438,762 | 3/1984 | Kyle . |
| 4,473,069 | 9/1984 | Kolmert . |
| 4,616,638 | 11/1986 | Griggs ...................................... 606/65 |
| 4,622,959 | 11/1986 | Marcus . |
| 4,657,001 | 8/1987 | Fixel . |
| 4,697,585 | 10/1987 | Williams . |
| 4,733,654 | 3/1988 | Marino . |
| 4,776,330 | 10/1988 | Chapman et al. . |
| 4,973,332 | 11/1990 | Kummer .................................. 606/65 |
| 4,988,350 | 1/1991 | Herzberg ................................. 606/65 |
| 5,041,114 | 8/1991 | Chapman et al. . |

FOREIGN PATENT DOCUMENTS

| | | |
|---|---|---|
| 867422 | 2/1953 | Germany . |
| 918531 | 9/1954 | Germany . |
| 1026786 | 7/1983 | U.S.S.R. . |

*Primary Examiner*—David Isabella
*Attorney, Agent, or Firm*—Knobbe, Martens, Olson & Bear

[57] ABSTRACT

A modular implant for use in stabilizing femoral bone disorders resulting from injury, disease or congenital defects. In one embodiment the implant has an upper side plate with a widened head and a angled barrel, and a lower side plate adapted to be engaged with the upper side plate in a tongue and groove configuration. The side plates, once engaged, conform with the cortical wall of the femur.

15 Claims, 3 Drawing Sheets

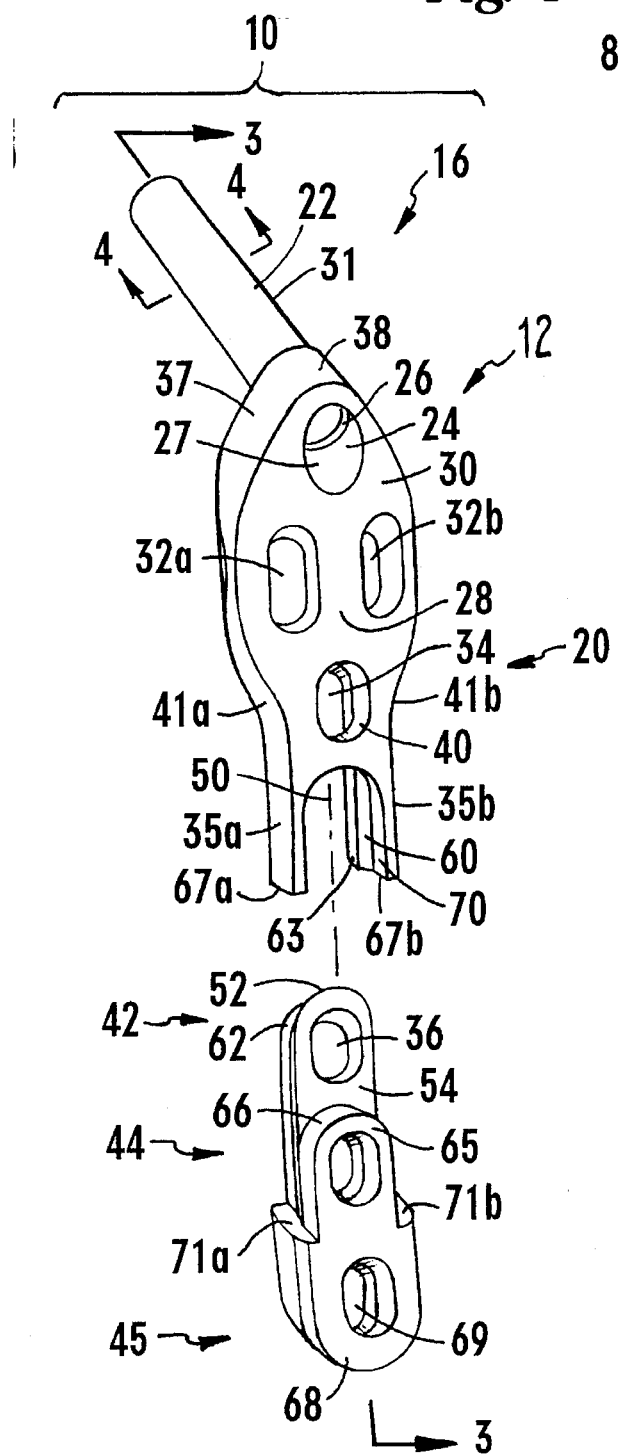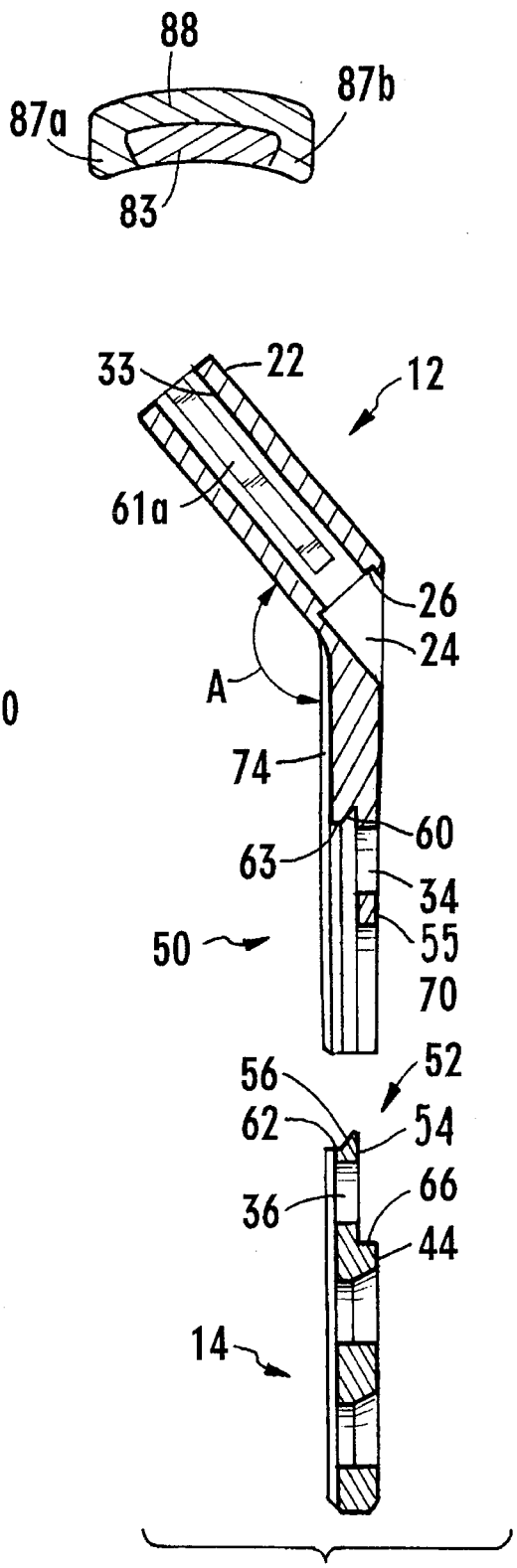
Fig. 1
Fig. 2
Fig. 3

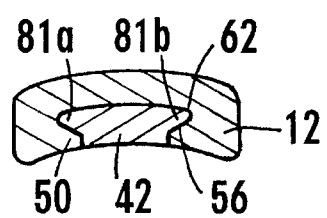
Fig. 4
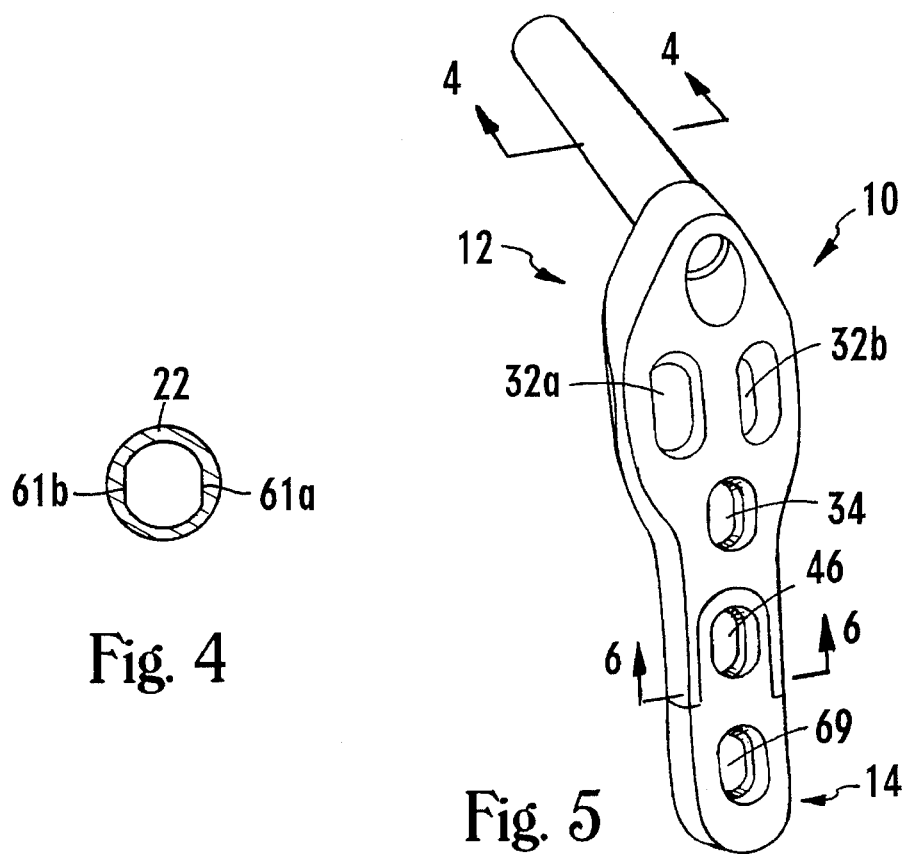
Fig. 5
Fig. 6
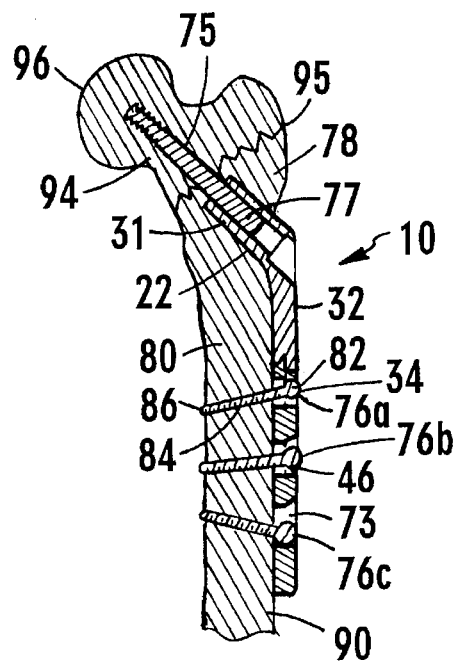
Fig. 7

MODULAR FEMUR FIXATION DEVICE

This application is a continuation of application Ser. No. 07/946,742, filed Sep. 16, 1992 now abandoned.

BACKGROUND OF THE INVENTION

The present invention relates to orthopedic implants, and more particularly to implants of the femur.

One of the most frequently performed orthopedic surgical procedures involves implantation of devices designed to stabilize femoral fractures. These devices stabilize fractures of the femoral neck, intertrochanteric and subtrochanteric regions, and distal femoral condyles. Fractures which might once have left a person wheel-chair bound, can now be effectively treated with femoral implants.

Four classes of intertrochanteric fractures are currently treated with implants. A Type I fracture is a simple fracture across the intertrochanteric area without any bone displacement. Type II fractures are also across the intertrochanteric area, but the head and upper trochanteric segment are additionally displaced. A Type III fracture is unstable and more complex, usually having fracture lines in the lesser trochanteric area. The most severe fractures, Type IV, involve fragments in the area of the lesser trochanter and may extend into the subtrochanteric area. These fractures are the most difficult to reduce to a stable position.

In Type III and IV intertrochanteric fractures, large unstable bone fragments exist in the lesser trochanteric area. Fracture alignment in these severe breaks is difficult to maintain. Excessive collapse can occur resulting in a shortening of the femur (loss of leg length) leading to poor clinical results.

Implants are designed to provide an internal splint which holds the fracture in alignment while healing occurs. Some more recent implants have additional components for stabilizing fractures of the femoral shaft.

Current designs use an elongated lag screw with a distal threaded portion that is advanced through the intertrochanteric area and femoral neck finally gripping the femoral head. The lag screw of these designs slides inside a hollow barrel which allows pressure across the fracture as weight bearing occurs. The hollow barrel is part of a cortical side plate called a barrel plate. The plate portion of the barrel plate is attached to the cortical wall, and the barrel portion extends into the trochanteric area of the femur.

These early femoral lag screws and barrel plates allowed for a much more rapid patient recovery by providing internal support for hip fractures. The elongated lag screw was engaged in the barrel providing a telescoping means for final fracture reduction and compression at the fracture site.

Other types of femoral implants have comprised, in addition to the lag screw, an intramedullary rod or cortical side plate (see, for example, U.S. Pat. No. 4,776,330 to Chapman, et al). In the system described by the Chapman et al. patent, the intramedullary rod provided stabilization for subtrochanteric and femoral shaft fractures. The cortical side plate of Chapman et al. could be used with a lag screw and lower removable extension plate of varying lengths to provide stability for trochanteric fractures. The side plate was fastened to the femur with cortical screws, while the barrel held the lag screw.

The Chapman, et al. implant could be used where femoral neck or intertrochanteric fractures were combined with subtrochanteric or shaft fractures in a single injury. With this system, the side plate could be extended in length with a lower removable portion being slidably engaged with the upper side plate. The lower portion normally provided the surgeon with additional mounting holes for attaching the lower portion to the cortical surface of the shaft. The lower side plates were slidably engaged with the upper side plates by various methods including a "dovetail" construction shown herein as FIG. 1.

In previous designs, such as the "dovetail" the lower side plate was uniformly thinner in size than the upper side plate and therefore inherently possessed less tensile strength. This strength limitation is undesirable in implant devices that need to withstand heavy bending forces.

By choosing between various embodiments of the lower slide plate, the physician could then select the proper number of mounting holes appropriate for the type of fractures of the particular patient's femoral shaft. For example, more distal shaft fractures would require longer lower plate extensions. The interchangeability of the lower side plate gave the physician a greater range of implant embodiments from which to choose for any given femoral fracture.

In some unstable fractures, large segments of the medial wall are broken loose in the area of the lesser trochanter. Devices which are currently available do not provide screw hole positions that allow these loose fragments to be stabilized.

Accordingly, it would be an important improvement in the art to provide a femoral implant which provides a wide angle where the screws can be used to stabilize bone fragments in the lesser trochanter area. In addition, it would be advantageous to have a lower side plate which, when slidably engaged with the upper slide plate, locks into position and has a design which provides greater tensile strength to help prevent bending and breakage.

SUMMARY OF THE INVENTION

The present invention is a femoral implant comprising upper and lower side plates designed for attachment to the outer cortical wall of a bone. In one preferred embodiment, the bone is the femur bone of a human. In other preferred embodiments, the implant is designed to stabilize the upper femur, fractures of the hip, and lower femoral fractures about the femoral condyles.

The upper side plate of the inventive implant has a head portion and an elongated hollow cylindrical barrel. The barrel is positioned at an oblique angle with respect to the head so as to be inserted inside a passage reamed out of the intertrochanteric region of the femur and thereby provide stability when used with an elongated lag screw for internal fixation. It can be appreciated that the barrel could be positioned at different angles with respect to the head ranging from 130° to 150° for upper femoral implants and 90° to 105° for lower condyle implants.

An internal fixation device as defined herein can utilize a nail, expansion bolt, or the most preferred embodiment, a lag screw disposed in a cylindrical barrel. The lag screw type of device is implanted prior to mounting the barrel plate, which is slid over and surrounds the lag screw.

To impede rotation of the lag screw once the barrel has been place over its protruding end, one preferred embodiment of the inventive implant has flat faces formed on the inner surface of the barrel designed to align with matching flat surfaces on the lag screw. Other embodiments comprise barrel plates without flat faces, allowing the lag screw to freely rotate. These two embodiments of the barrel plates can advantageously use the same lower plate extensions interchangeably.

One embodiment of the present invention provides a more sturdy implant than those previously disclosed by having a "tongue and groove" type attachment means for slidably engaging the upper and lower side plates. This configuration provides a uniform thickness throughout the upper and lower cortical side plates advantageously imparting greater strength to the implant when in use. Upon engagement of the upper and lower side plates, the inner and outer surfaces are substantially continuous throughout the region adjacent either side of the engagement location.

Another embodiment of the present invention comprises an upper side plate with a head portion substantially larger than the diameter of the barrel advantageously providing enough room for adjacent offset lag screw mounting holes. The offset position of the adjacent mounting holes allows the wide angle approach that is necessary to secure and stabilize the fractured portions of the medial femoral wall in the area of the lesser trochanter. The fragments can be secured with cortical or cancellous bone screws, nails, or expansion pegs.

In one preferred embodiment of the present invention, the offset mounting holes in the enlarged head portion are directly adjacent one another, and comprise elliptical holes traversing the upper side plate head. The elliptical mounting holes extend from the top portion of the upper side plate head substantially to the bottom portion of the side plate head providing a plurality of positions for the surgeon to insert a cortical or cancellous bone screw. Other preferred embodiments of the widened head portion could have multiple offset mounting holes.

The widened upper side plate head of the preferred embodiment thereby provides a distinct advantage over any of the previous femoral implants by giving the surgeon a greater choice of vertical positions and angles available for inserting the lag screws.

BRIEF DESCRIPTION OF THE FIGURES

FIG. 1 is a cross-sectional view of a prior art "dovetail" mechanism for slidably engaging the upper and lower side plates.

FIG. 2 is an exploded perspective view of one preferred embodiment of the femoral implant of the present invention.

FIG. 3 is a cross-sectional view of a preferred embodiment of the femoral implant of the present invention taken along the line 3—3 of FIG. 2.

FIG. 4 is a cross-sectional view of the barrel of the femoral implant taken along the line 4—4 of FIG. 2.

FIG. 5 is a perspective view of a preferred embodiment of the invention, illustrating the lower side plate slidably engaged with the upper side plate.

FIG. 6 is a cross-sectional view of the tongue and groove engagement of the upper and lower side plates, taken along the line 6—6 of FIG. 5.

FIG. 7 is a cross-sectional view of a preferred embodiment of the implant, attached to a femoral shaft. A lag screw is inserted through the barrel of the implant into the femoral head.

DETAILED DESCRIPTION

Figure 8:
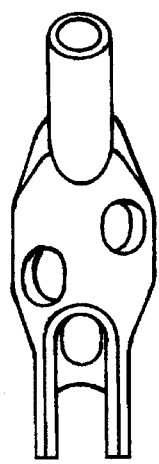
FIGS. 8–12 are a front elevational views of other preferred embodiments of the head portion of the present invention.

Referring to FIG. 2, a femoral implant 10 comprises an upper side plate 12 and a lower side plate 14. Upper side plate 12 has a top end 16 comprising an angled hollow tubular barrel 22 with an outer cylindrical wall 31 and inner surface 33 (Shown in FIG. 3). The preferred diameter of the outer cylindrical wall 31 is about 0.50 inches. The preferred diameter of the inner wall 33 is about 0.355 inches.

Except as noted otherwise, the various preferred embodiments of the present invention are comprised of a physiologically inert titanium, such as titanium 6/4 (6 Aluminum/4 Vanadium). Femoral implants produced with alternative physiologically inert materials (ie: stainless steel, calbolt chrome, or other F.D.A. approved implant materials) are also within the scope of the present invention.

The tubular barrel 22 is permanently connected at its lower end to a head portion 30 of the upper side plate 12 at an angled orifice 24. The angled orifice 24 conforms to and surrounds the lower portion of the barrel 22 so as to define a through bore extending through the orifice 24 and along the length of the barrel 22. The barrel 22 extends through approximately 50% of the thickness of orifice 24 with the circular bottom of the barrel 22 defining an inner lip 26 formed by the inner barrel wall 33.

Below the angled orifice 24 of the upper side plate 12 is the main body 28 of the elliptical widened head portion 30. The elliptical head portion 30 has an inner and outer surface, the inner surface designed to contact the cortical wall. It can be appreciated that the inner and outer surfaces of the upper side plate head 30 are curved so as to match the mostly cylindrical form of the femur. The interaction of the inner surface of the upper side plate 12 and femoral cortical wall will be discussed below following the description of the preferred embodiment.

The main body 28 of the head portion 30 is preferably about 0.3 inches thick and, due to this thickness, has a sidewall 37 disposed around its upper and side periphery. The sidewall 37 is rounded and angled upward at a top exterior surface 38 partially covering the barrel 22 while it is engaged in the upper angled orifice 24 (See FIG. 2). Below the angled orifice 24, the main head body 28 widens to approximately twice the width of the barrel 22.

The main body 28 of the head 30 further comprises two adjacent vertically elliptical mounting holes 32a,b visually dividing the head 30 into thirds. Each mounting hole 32a,b is beveled, having a larger exterior circumference than interior circumference.

Each mounting hole 32 is positioned to give varied alternative locations for insertion of a mounting device such as a lag screw therethrough. In the preferred embodiment, mounting holes 32a,b are purposefully adjacent one another so as to provide lateral stability for the implant 10 when mounted to the femoral shaft. The mounting holes 32 are beveled inward providing a way to countersink the mounting devices (ie: lag screws or bone screws) used to attach the implant 10 to the femur.

Below the adjacent mounting holes 32a,b, the oblong head 30 narrows on both sides to define curves 41a,b. Disposed centrally between curves 41a,b and traversing the lower portion of the head 30 is a central mounting hole 34 providing the outer half of a means for affixing the upper side plate 12 to the cortical wall. Central mounting hole 34 is also used to reversibly engage the lower side plate 14 with the upper side plate 12. The inner half of the mounting hole will be discussed following the description of the upper side plate 12.

Below the central mounting hole 34 is a downwardly curved retaining wall 70 traversing and creating a passage through the lower portion 20 of the upper side plate 12. The periphery of the retaining wall 70 forms an inverted "U" shape extending from just below the central mounting hole 34 to the perpendicular bottom engagement walls 67a,b of the upper side plate 12. The retaining wall 70 thereby creates an opening at the bottom portion 20 of the upper side plate 12. It can be appreciated that in one preferred embodiment, the width of the upper side plate surrounding the central mounting hole 34 and retaining wall 70 is approximately one-half that of the main head body 28.

A beveled channel 60 extends upwardly along the interior edge of the side panels 35a,b, with the bottom edge of the channel 60 contacting the engagement walls 67a,b and with its upward portion forming a rounded groove just above and interior of the central mounting hole 34.

Disposed on the inner side of the beveled channel 60 is a lip 63 which defines the inner wall of the channel 60 and follows the periphery of the channel 60 from the engagement walls 67a,b to the rounded top groove (not shown). The lip 63 defines the outer circumference of a semi-circular opening on the inner surface of the bottom portion 20. The lowest portions of the retaining wall 70, channel 60, and lip 63 define the shape of the two engagement walls 67a,b. Each wall 67a,b runs perpendicular to the direction of the channel 60, and parallel to the direction of the mounting holes 32a,b, and 34.

Designed to slidably fit against the upper side plate channel 60, lip 63 and retaining wall 70, and abut the engagement walls 67a,b is a lower side plate 14 having an upper engagement tab 42. Defining the top periphery of the upper engagement tab 42 is a rounded tip 52 having a beveled wall 56 and non-beveled base 62. The wall 56 is beveled inward and traces the periphery of the inner edge of the tab 42. The non-beveled base 62 is disposed on the inner surface of the wall 56 and results in the formation of a lip circumscribing the outer edge of the tab 42.

Beginning at about 0.5 inches below the rounded tip 52 is a mating portion 44 disposed on the exterior surface 54 of the tip 52. The mating portion 44 has with a curved tip 65 approximately matching the curvature of the tab 42. The thickness of the lower side plate 14 at the position where the mating portion 44 is attached to the exterior surface 54 of the tab 42 is chosen to be approximately equal to the thickness of the upper side plate 12. It can be appreciated, and will be discussed later, that the engagement of the upper and lower side plates will thereby lead to the formation of a continuous smooth surface over the interior and exterior portions of both side plates.

Traversing the center of the mating portion 44 is a beveled mounting hole 46. Disposed below the tab 42 and mating portion 44 is a rounded bottom end 68 with side transverse flanges 71a,b. These flanges 71a,b are created by the larger width of the lower end 68 in relation to the mounting portion 44. The transverse flanges 71a,b face upward towards the tab 42 and providing a small flat surface whose use will be described below.

The bottom end 68 of the lower side plate 14 also has a beveled mounting hole 69 traversing its thickness and providing an additional position for insertion of a bone attachment device.

Now referring to FIG. 3, the cross-sectional view of the preferred embodiment illustrates the inner cylindrical surface 33 of the angled barrel 22 as having a pair of parallel opposing flat faces 61a,b (shown in more detail in FIG. 4). These faces 61 are formed in the inner surface 33 of the barrel 22. As will be discussed more fully hereafter, these faces 61 act in concert with corresponding flat faces on an implant device, such as an elongated lag screw, to prevent any rotation of the elongated lag screw after it is fixed into position.

As can also be appreciated by the cross-sectional view of FIG. 3, the combination of the non-beveled base 62 and beveled wall 56 forms a lip circumscribing the tip 52 and sides of the mating tab 42. It is also apparent that upon mating of the tab 42 into the engagement channel 50, the aforementioned lip conforms to and slides flush against an inner semicircular lip 63 of the upper side plate. The receiving channel 60 and lip 63 of the upper side plate thereby define a periphery around the beveled wall 56 and base 62 when engaged.

Referring back to FIG. 2, during engagement of the upper and lower side plates 12 and 14 (as illustrated by FIG. 5), the outer surface 54 of the tab 42 contacts the inner surface 55 surrounding the central mounting hole 34. In addition, the beveled edge 56 of the tab 42 engages the receiving channel 60 disposed inside the channel 50. It can be appreciated that the receiving channel 60 is beveled at an angle which matches the beveled surface 56 of the tab 42 upon contact. The receiving channel 60 thereby provides a means for inhibiting the inward and lateral movement of the tab 42 once engaged in the channel 60. The beveled surface 56 and channel 60, when engaged with one another, add strength to the implant and help prevent separation due to lateral forces applied on the device. The non-beveled base 62 likewise mates with the lip 63 of the upper side plate when the tab 42 slidably engages the bottom end 20 of the upper side plate 12. The engagement of the non-beveled base 62 and lip 63 also provide strength and stability to the device preventing separation due to lateral forces on the implant.

As shown in FIG. 6, the tongue and groove configuration of the inventive implant provides more strength in the lateral direction than the prior art "dovetail" design (FIG. 1). The outward flanges 81a,b formed by the beveled surface 56 and non-beveled base 62 make the tab 42 very difficult to force laterally out of the channel 50. In addition, the overall thickness of the lower portion 14 is substantially the same as the upper side plate 12 giving it more tensile strength. As can be appreciated by FIG. 1 showing the prior art "dovetail" design, a small lateral force on the insert 83 would cause it to crack or break completely, making it a less desirable implant.

Referring again to FIG. 2, the lower side plate 14 also has a semicircular wall 66 defining a periphery around the mating portion 44. The wall 66 slides against and contacts the lower rounded retaining wall 70 of the upper side plate 12 upon engagement. This contact impedes forward movement of the lower side plate, and provides lateral strength and stability to the lower side plate. The lateral stability is due to the design of the retaining wall 70 which substantially surrounds the mating portion 44 on three sides.

Additionally, transverse flanges 71a,b contact the bottom surfaces 67a,b of the lower side plate 14 upon engagement providing a further method of preventing forward compressive pressure of the upper and lower side plates.

The multiple wall contact of the tab 42 into the channel 50 provides additional strength in the outward direction as compared to a "dovetail" type of engagements seen in previous designs. As can be appreciated, lateral strength in the outward direction can be very advantageous once the implant is mounted to the femoral bone. The added strength provided by the tongue and groove engagement of the present invention acts as an advantageous support preventing implant breakage and failure.

In Vivo Use of the Present Invention

As will be appreciated by reference to FIG. 7, in using one preferred embodiment of the present invention, the surgeon first drills a longitudinal passage from the great trochanter 78 towards the femoral head 96, completely traversing the femoral neck 94. Advantageously, this passage is of such a diameter that the outer cylindrical wall 31 of the hollow tubular barrel 22 can fit internally and advance along the line of the passage towards the femoral head 96 when the implant 10 is affixed to the outer cortical wall 90 of the femur (FIG. 7).

The intertrochanteric passageway created by the surgeon is advantageously therefore only slightly wider than the outer wall 31 of the tubular barrel 22. After drilling the intertrochanteric passage, the surgeon places the elongated lag screw in the femoral head through the pre-reamed passageway.

The surgeon threads an extended lag screw 75 into the femoral head 96 through a fracture 95. The surgeon then slides the barrel 22 of the implant 10 over the end 77 of the lag screw. As discussed above, the hollow tubular barrel 22 contacts the head 30 at an angle of approximately 135° reproducing the angle formed by the vertical femoral shaft and the longitudinal axis of the femoral neck 94. Therefore, with the end 77 of the lag screw 75 slid inside the barrel 22, the inner surface of the implant 10 will be in contact the cortical surface of the femur.

The elongated lag screw 75 is meant to slide free in the longitudinal direction of the barrel 22 of the femoral implant thereby allowing compression of the fracture upon weight bearing. In one preferred embodiment, the sides of the non-threaded portion 77 of the elongated lag screw 75 possesses parallel flat faces that align with and conformably match the faces 61a,b on the inner cylindrical wall 33 of the barrel. Once the faces on the outer surface of the rearward portion 77 of the elongated lag screw 75 and the faces 61a,b are slidably engaged, rotation of the elongated lag screw 75 inside the barrel 22 is impeded. In this manner the surgeon can ensure that the elongatd lag screw, once inserted, will not rotate.

After sliding the barrel 22 over the lag screw 75, the lower side plate 14 is slidably engaged with the upper side plate 12 (FIG. 2). During the engagement process, the upper tip 52 of the tab 42 slides beneath the retaining wall 70 and under the central mounting hole 34. The mounting hole 36, located centrally in the tab 42, aligns on the interior side of the central mounting hole 34 creating one passage from the outer surface to the femoral shaft.

While the tip 52 slides beneath the retaining wall 70, the beveled wall 56 engages and slides along the surface of the receiving channel 60. Simultaneously the non-beveled base 62 slides along the inner lip 63 of the upper side plate. Once the engagement is complete, the outer wall 66 of the upper mating portion 44 contacts and mates with the retaining wall 70. At the same time that the outer wall 66 contacts the retaining wall 70, the transverse flanges 71a,b contact the engagement walls 67a,b further impeding any upward movement of the lower side plate 14 into the upper side plate 12.

After engagement of the upper and lower side plates, a bone screw is placed through central hole 46 (see FIG. 5) fastening the implant to the femur while simultaneously securing the upper side plate 12 to the lower side plate 14. The surgeon next places bone screws in all the remaining holes of the lower side plate 14, below hole 46.

Finally, lag screws are placed in the elliptical mounting holes 32a,b. In the preferred embodiment, as shown in FIG. 2, the surgeon can place lag screws in a plurality of positions inside the elliptical mounting holes 32a,b to secure fragments of the medial wall in the area of the lesser trochanter. When these fragments are reduced and secured there is less chance for collapse which results in leg shortening and additional stresses on the implant that can lead to implant failure. Moreover, multiple lag screws can be placed into each of the mounting holes 32a,b providing further flexibility for the surgeon.

An additional benefit of the elliptical adjacent mounting holes is that fragments of the lesser trochanter can be buttressed back into position along the femur. Prior implants with narrow heads could not effectively be used to buttress lesser trochanteric fractures because of the angle required to properly position the lag screw. The widened head and elliptical mounting hole of the inventive implant provides a means for being able to reach the angled lesser trochanteric region, thereby efficiently buttressing it to the medial wall.

In addition to the advantage provided by the offset mounting holes, a widened head portion inherently imparts greater stability for fractures that are directly adjacent to the head portion of the femur. By having a larger femoral surface in contact with the implant, the widened head gives greater stability to the cortical surface directly below the upper side plate surface.

The passage created by the upper central mounting hole 34 and lower mounting hole 36 provides a means for placing an additional bone screw into the femoral shaft while simultaneously attaching the upper and lower side plates together. The tongue and groove mating provided by the beveled wall 56 engaging the receiving channel 60 provides a laterally stronger implant than previous designs.

As described in the background section, a majority of previous lower side plate designs were made to engage the upper side plate in a "dovetail" type of attachment. This form does not have the bending strength of the present invention and therefore can provide a less desirable implant choice for the surgeon.

As illustrated in FIGS. 5 and 7, after engaging the lower side plate 14 into the upper side plate 12, bone screws are placed in the mounting holes 34, 46, and 69 providing a means for securely attaching the femoral implant 10 to the cortical wall 90 of the femoral shaft 80.

Alternate Preferred Embodiments of the Present Invention

Figure 9:
Figure 10:
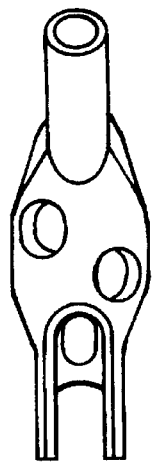
Figure 11:
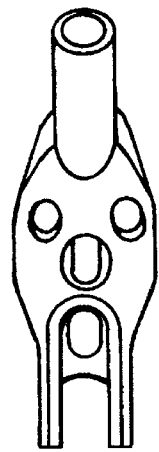

The widened head embodiment discussed above has elliptical adjacent mounting holes for inserting a plurality of lag screws. However, other embodiments of the mounting holes are also contemplated as illustrated by FIGS. 8–12. In FIGS. 8 and 9, the mounting holes are offset, with one hole in a higher position than the other. The offset hole arrangements allow the surgeon to select a specific embodiment for maximizing security and stability in particular situations. As with the embodiments described previously, this embodiment also provides the ability to attach broken bone fragments and draw them to a reduced position. FIGS. 10 and 11 illustrate two additional configurations of devices with hole arrangements permitting flexibility in their use. Other configurations of offset hole arrangements are also contemplated as falling within the scope of the invention.

As can be appreciated by FIG. 2, the offset positions of the elliptical mounting holes 32a,b in the wide head 30 of the upper side plate 12 gives the surgeon better methods to secure the bone fragments found in femoral fractures. This configuration of offset mounting holes disposed in a widened head provides a significant advantage over previous implants that only had a linear series of mounting holes. With previous designs, the surgeon was unable to effectively insert a lag screw into bone fragments so as to correct the instability that leads to leg shortening and other unfavorable clinical results. There was therefore no effective method of stabilizing these types of fractures with an implant.

Other embodiments of the present invention could comprise specific portions of the advantageous features of the above-described embodiments. For example, an implant with a widened upper side plate head could be slidably attached to a lower side plate by any means know to those in the art (eg: dovetail) and still be within the scope of the present invention.

Figure 12:
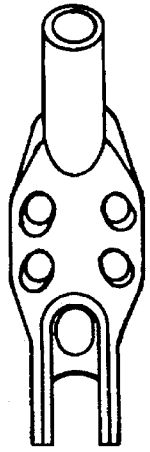

Alternatively, embodiments of the present invention, such as those shown in FIG. 12, wherein the inventive tongue and groove slidable attachment is used in an implant without a widened head, define a valuable improvement in the technology and fall within the scope of the present invention. One such device would comprise an upper side plate with a narrow head having a slidable tongue and groove attachment to the lower side plate. This implant would be used in hip fractures that do not have medial fragments.

In addition to the described embodiment of the lower side plate having two mounting holes, alternative embodiments having an extended mounting extension with multiple transverse bone screw holes are also anticipated. Embodiments comprising, for instance, 3 to 14 bone screw holes are contemplated. Such an extended lower side plate may be necessary in femoral shaft fractures.

In addition, in one preferred embodiment, the angle formed by the oblique attachment of the barrel with the upper side plate head can comprise any angle between approximately 130° and 150°. As discussed above, a 135° is preferred since it most closely matches the in vivo angle formed by the femoral shaft and neck, but all angles between about 130° and 150° are within the scope of this invention.

Figure 13:
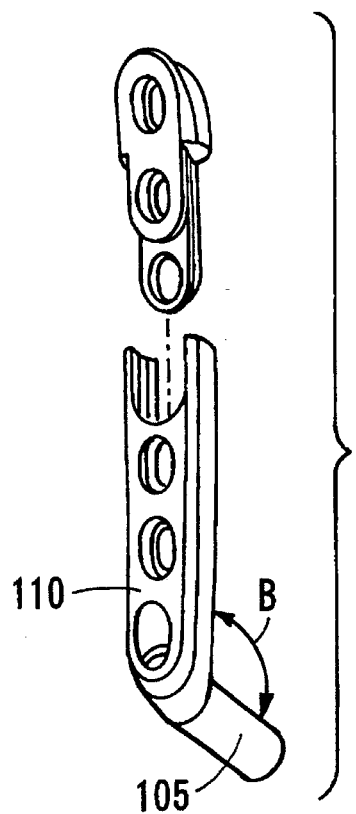
FIG. 13 is a perspective view of an implant device designed to stabilize the lower condyle region of the femur.

Other preferred embodiments of the present device include implants with the inventive widened head, or tongue and groove engagement for use in with fractures other than those of the upper femoral region. For example, implants to stabilize fractures of the lower femoral condyle region are within the scope of the present invention. In this alternate embodiment (FIG. 13) the barrel 105 is positioned at an angle B of about 95° relative to the head portion 110. This angle provides the most advantageous direction for insertion of a elongated lag screw to stabilize a lower condyle fracture. Other angles of between 85° and 105° are also anticipated to be encompassed by this embodiment of the present invention. In a fashion similar to that discussed above for stabilization of an upper femoral fracture, elongated lag screws, side plates, and cortical or callous bone screws can be used to stabilize lower condyle fractures. It should be noted that in this embodiment, the barrel plate is mounted upside down from the mounting position of the upper femoral side plate. In this instance, the barrel plate portion is shaped to fit the contour or the condyle region. The extended lower side plate (positioned above the barrel plate in this embodiment) can be the same as that described above for the upper femoral implant. This modularity is one of the great advantages of the present implant system.

The femoral implant disclosed herein provides an advantageous way of correcting and stabilizing fractures of the upper end of the femur. These fractures can be classified into fractures of the neck, intertrochanteric, or subtrochanteric areas.

In addition to fractures at the upper end of the femur, fractures of the shaft may also occur simultaneously with the direct or indirect trauma that caused the proximal fracture. The added strength of the tongue and groove design of the preferred embodiment femoral implant is one great advantage where hip and shaft fractures occur simultaneously.

The tongue and groove conformation of the present femoral implant significantly increases bending strength at the mating point as compared to previous implants. In contrast, an implant with no tongue and groove conformation wherein the lower side plate simply slides below the upper side plate, contains less tensile strength.

In the inventive implant, the tongue and groove conformation provides tensile strength to prevent bending which prevents added pressure on the bone screws affixing the upper and lower plates. In addition to the above stated advantageous tongue and groove conformation of the preferred embodiment, the wide head of the upper side plate with adjacent offset mounting holes discussed above allows the surgeon to secure bone fragments found in femoral fractures.

As can be appreciated by the preceding discussion of alternated preferred embodiments of the present invention, the inventive implant provides a very modular system for the surgeon. For example, a widened head portion and extended lower side plate could be used in unstable intertrochanteric and subtrochanteric fractures while short plate extensions with a standard upper plate (FIG. 12) would be used for stable intertrochanteric or femoral neck fractures. The tongue and groove configuration of the inventive implant would provide greater strength in the lateral direction, while the extended side plate could be used to secure varying locations of femoral shaft fractures.

Additionally, with the various angled barrel plates (such as 130°, 135°, 140°, 145°, and 150°), a device such as a distal condyle barrel plate with a widened head allows the physician many options. The interchangeability of the upper and lower side plate embodiements (discussed above) also allows for a reduced inventory while retaining a high degree of implant flexibility.

The invention may be embodied in other specific forms without departing from its spirit or essential characteristics. The described embodiment is to be considered in all respects only as illustrative and not restrictive and the scope of the invention is, therefore indicated by the appended claims rather than by the foregoing description. All changes which come within the meaning and range of equivalency of the claims are to be embraced within their scope.

We claim:

1. An implant for the fixation of a bone fracture comprising:

an upper side plate with an inner surface, an outer surface, at least one mounting hole, a beveled receiving channel located below a cylindrical barrel and a head, wherein said barrel comprises an elongated hollow cylinder positioned at an oblique angle with respect to said head so that when the inner surface of said head is mounted against the cortical wall of a bone said barrel is substantially aligned with the longitudinal axis of the femoral neck; and a lower side plate with an inner and outer surface, said lower side plate also having a beveled outward flange slidably engagable at an engagement location with said beveled receiving channel in said upper side plate, said beveled outward flange being thinner than any other part of the lower side plate, and said lower side plate including at least one mounting-hole for mounting said lower side plate to a cortical wall.

2. The implant of claim 1 wherein the inner and outer surfaces of the implant are substantially continuous throughout the region adjacent either side of the engagement location.

3. The implant of claim 1 wherein the inner surface of the upper and lower side plates of said implant is curved to conform with the cortical wall of the proximal femur.

4. The implant of claim 2 wherein said inner and outer surfaces are curved to conform with the substantially cylindrical shape of the bone.

5. The implant of claim 1 wherein said inner and outer surfaces are curved to conform with the substantially cylindrical shape of the bone.

6. the implant of claim 2 wherein the distance between the inner and outer surfaces of the upper and lower side plates formed by the engaged side plates is substantially uniform in the regions adjacent either side of a location where the engagement is accomplished.

7. The implant of claim 1 wherein said barrel has internal flat faces.

8. An implant for the stabilization of a fractured femur bone comprising:

an upper side plate with inner and outer surfaces, a top end and a bottom end wherein a longitudinal axis extends between said top end and said bottom end, a cylindrical barrel mounted to said inner surface, adjacent said top end, at an oblique angle with respect to said inner surface;

an enlarged head portion substantially wider than said barrel with offset mounting holes located on either side of the longitudinal axis of said upper side plate and below said barrel, and a lower engagement means [and wherein said barrel comprises an elongated hollow cylinder positioned at an oblique angle with respect to said enlarged head so as to be in substantial alignment with the longitudinal axis of the femoral neck; and a lower side plate with an inner and outer surface, removably attached with said upper side plate defining an engagement location, and having at least one mounting hole for attachment to the femoral shaft.

9. The implant of claim 8 wherein the upper and lower surfaces of the implant are substantially continuous throughout the region adjacent either side of the engagement location.

10. The implant of claim 8 wherein the distance between the inner and outer surface of the engaged side plates is substantially uniform in the regions adjacent either side of a location where the engagement is accomplished.

11. The implant of claim 9 wherein said upper and lower surfaces are curved to conform with the substantially cylindrical shape of the femur.

12. The implant of claim 8 wherein said barrel has internal flat faces.

13. The implant of claim 8 wherein said offset mounting holes comprise two adjacent elliptical mounting holes.

14. An implant for the fixation of a femoral fracture comprising:

an upper side plate having an inner and an outer surface, a cylindrical barrel and a head, wherein said barrel comprises an elongated hollow cylinder positioned at an oblique angle with respect to said head so that when said head is mounted against the cortical wall of a femur said barrel is substantially aligned with the longitudinal axis of the femoral neck; and a lower side plate having an inner and an outer surface slidably engaged with said upper side plate at a point below said hollow cylinder such that, when the upper and lower side plates are fully engaged, the distance between the inner and outer surfaces formed by the engaged side plates is substantially uniform in those regions adjacent either side of a location where the engagement is accomplished, and wherein the lower side plate includes at least one mounting-hole for mounting said lower side plate to a femoral cortical wall.

15. The implant of claim 14, wherein the lower side plate has a beveled outward flange and is slidably engaged with a beveled receiving channel in the upper side plate.

* * * * *